United States Patent
Baudy et al.

(10) Patent No.: US 7,879,825 B2
(45) Date of Patent: Feb. 1, 2011

(54) DERIVATIVES OF [2-(8,9-DIOXO-2,6-DIAZABICYCLO[5.2.0]NON-1(7)-EN-2-YL)ALKYL] PHOSPHONIC ACID AND METHODS OF USE THEREOF

(75) Inventors: Reinhardt B. Baudy, Buckingham, PA (US); John A. Butera, Clarksburg, NJ (US)

(73) Assignee: Wyeth LLC, Madison, NJ (US)

( * ) Notice: Subject to any disclaimer, the term of this patent is extended or adjusted under 35 U.S.C. 154(b) by 855 days.

(21) Appl. No.: 11/757,006

(22) Filed: Jun. 1, 2007

(65) Prior Publication Data

US 2007/0225257 A1  Sep. 27, 2007

Related U.S. Application Data

(63) Continuation of application No. 10/820,216, filed on Apr. 7, 2004, now Pat. No. 7,253,153.

(60) Provisional application No. 60/461,490, filed on Apr. 9, 2003.

(51) Int. Cl.
  A61P 25/00 (2006.01)
  A61K 31/675 (2006.01)
  C07D 223/00 (2006.01)
(52) U.S. Cl. ........................ 514/80; 540/542
(58) Field of Classification Search ............. 514/80; 540/542

See application file for complete search history.

(56) References Cited

U.S. PATENT DOCUMENTS

| | | | |
|---|---|---|---|
| 5,124,319 A | 6/1992 | Baudy et al. | 514/80 |
| 5,168,103 A | 12/1992 | Kinney et al. | 514/221 |
| 5,240,946 A | 8/1993 | Kinney et al. | 514/364 |
| 5,624,898 A | 4/1997 | Frey, II | 514/12 |
| 5,990,307 A | 11/1999 | Asselin et al. | 540/542 |
| 6,011,168 A | 1/2000 | Asselin et al. | 558/172 |
| 6,451,848 B1 | 9/2002 | Behl et al. | 514/468 |
| 2003/0114444 A1 | 6/2003 | Brandt et al. | 514/221 |
| 2004/0082543 A1 | 4/2004 | Cheung | 514/80 |
| 2005/0004079 A1 | 1/2005 | Benjamin et al. | 514/80 |
| 2005/0142192 A1 | 6/2005 | Benjamin et al. | 424/464 |

FOREIGN PATENT DOCUMENTS

| | | |
|---|---|---|
| EP | 0 496 561 A2 | 7/1992 |
| EP | 0 778 023 A1 | 6/1997 |
| EP | 0 994 107 A1 | 4/2000 |
| WO | 98/15542 A1 | 4/1998 |
| WO | 99/06417 A1 | 2/1999 |
| WO | 99/64041 A1 | 12/1999 |
| WO | 03/031416 A2 | 4/2003 |
| WO | 2004/039371 A2 | 5/2004 |

OTHER PUBLICATIONS

Abou-Gharbia, Abstract Paper, *Am. Chem. Soc.*, 2001, 221st MEDI 202.
Abrahams et al., *Emerging Drugs*, 2000, 5(4), 385-413.
Baron et al., *Psychopharmacology*, 1995, 118, 42-51.
Baudy et al., *J. Med Chem*, 1993, 36, 331-342.
Baudy et al., *J. Med. Chem.*, 2001, 44, 1516-1529.
Behl, C.R. et al., *Advanced Delivery Reviews*, 29, 117-133, 1998.
Bennett, G.J. et al., *Pain*, 1988, 33, 87-107.
Bennett, *Journal of Pain & Sympton Management*, 2000, 19(Suppl.), S2-S6.
Boyce, S. et al., *Neuropharmacology*, 1999, 38, 611-623.
Bradford et al., *Stroke & Cerebral Circulation*, 1998, Abstract.
Brandt et al., *Journal of Pharmacology & Experimental Therapeutics*, 2001, 296(3), 939-946.
Brown et al., "N-Methyl-D-Aspartate Receptor (NMDA) Antagonists as Potential Pain Therapeutics," *Current Topics in Medicinal Chemistry*, 2006, 6(8), 749-770.
Chaplan et al., *Journal of Neuroscience Methods*, 1994, 53, 55-63.
Chaplan et al., *Pharmacology & Experimental Therapeutics*, 1997, 280(2), 829-838.
Chaplan, S.R. et al., *Journal of Neuroscience Methods*, 1994, 53, 55-63.
Childers et al., *Drugs of the Future*, 2002, 27(7), 633-638.
Chizh et al., *Trends in Pharmacological Sciences*, 2001, 22(12), 636-642.
Eisenberg, E.J. et al., *Nucleosides, Nucleotides & Nucleic Acids*, 2001, 20(4-7), 1091-1098.
Farquhar, D. et al., *Journal of Medicinal Chemistry*, 1994, 37(23), 3902-3909.
Farquhar, D. et al., *Journal of Pharmaceutical Sciences*, 1983, 72(3), 324-325.
Fix et al., *Experimental Neurology*, 1998, 123, 204-215.
France et al., *European Journal of Pharmacology*, 1989, 159, 133-139.
France et al., *Journal of Pharmacology & Experimental Therapeutics*, 1991, 257(2), 727-734.
Frankova, D. et al., *Nucleosides & Nucleotides*, 1999, 18(4/5), 955-958.

(Continued)

Primary Examiner—Brenda L Coleman
(74) Attorney, Agent, or Firm—Joel Silver

(57) ABSTRACT

Compounds of formula (I) or pharmaceutically acceptable salts thereof are provided

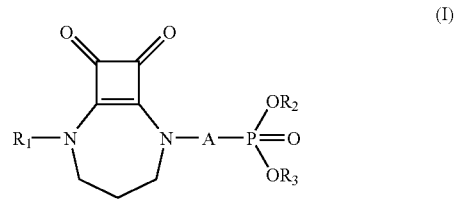

(I)

where at least one of $R_2$ or $R_3$ is not hydrogen. The compounds of the present invention are N-methyl-D-aspartate (NMDA) receptor antagonists and are useful in treating a variety of conditions present in a mammal that benefit from inhibiting the NMDA receptor.

6 Claims, No Drawings

OTHER PUBLICATIONS

Hao et al., *Pain*, 1996, 66, 279-285.
Hatse, S. et al., *Molecular Pharmacology*, 1996, 50(5), 1231-1242.
Herrling, P.L., Academic Press, Chapter 1, 1-6 (1997).
Hewitt, D., *The Clinical Journal of Pain*, 2000, 16, S73-S79.
Hussain, A., *Advanced Delivery Reviews*, 1998, 29, 39-49.
Kahn, S.R. et al., *Tetrahedron Letters*, 1999, 40(4), 607-610.
Karlsten et al., *Drugs & Aging*, 1997, 11(5), 398-412.
Kinney et al., *J. Med. Chem.*, 1998, 41, 236-246.
Kinney, W.A. et al., *Journal of Medicinal Chemistry*, 1992, 35(25), 4720-4726.
Kristensen et al., Database Biosis, Biosciences Information Service, Abstract XP002228851, 1992.
Kristensen et al., *Pain*, 1992, 51, 249-253.
Lefebvre, I. et al., *Journal of Medicinal Chemistry*, 1995, 38(20), 3941-3950.
Lipton, "Failures and Successes of NMDA Receptor Antagonists: Molecular Basis for the Use of Open-Channel Blockers like Memantine in the Treatment of Acute and Chronic Neurologic Insults," *The Journal of the American Society for Experimental Neuro Therapeutics*, 2004, 1(1), 101-110.
Lombaert, S.D. et al., *Journal of Medicinal Chemistry*, 1994, 37(4), 498-511.
McRoberts et al., *Gastroenterology*, 2001, 120(7), 1737-1748.
Menniti, F. et al., *European Journal of Pharmacology*, 1997, 331, 117-126.
Millan et al., *Neuroscience Letters*, 1994, 178, 139-143.
Mori et al., *Behavioural Brain Research*, 2001, 119, 33-40.
Mosconi, T. et al., *Pain*, 1996, 64, 37-57.
Mulato, A.S. et al., *Antimicrobial Agents and Chemotherapy*, 1998, 42(7), 1620-1628.
Mutel, V. et al., *Journal of Neurochemistry*, 1998, 70, 2147-2155.
Naesens, L. et al., *Antimicrobial Agents and Chemotherapy*, 1998, 42(7), 1568-1573.
Nicholson et al., *Behavioural Pharmacology*, 1998, 9, 231-243.
Olivar et al., *Pain*, 1999, 79, 67-73.
Oliyai, R. et al., *Nucleosides, Nucleotides & Nucleic Acids*, 2001, 20(4-7), 1295-1298.
Olney et al., *Science*, 1989, 244, 1360-1362.
Olney et al., *Science*, 1991, 254, 1515-1518.
Pal et al., *Burns*, 1997, 23(5), 404-412.
Parr, G.D., *Pharmacy International*, 1983, 4, 202-205.
Robbins, B.L. et al., *Antimicrobial Agents and Chemotherapy*, 1998, 42(3), 612-617.
Rogawski et al., *Trends in Pharmaceutical Sciences*, 1993, 14, 325-331.
Rogers, K., Wyeth-Perzinfotel (EAA-0090) NMDA Antagonist for the Treatment of Diabetic Neuropathy, 47 pages, presented on Jun. 9, 2004 at the SMI Pain Conference, London, England.
Rygh et al., *Pain*, 2001, 93, 15-21.
Sang, *Journal of Pain & Sympton Management*, 2000, 19(Suppl.), S21-S25.
Starrett, J.E. et al., *Journal of Medicinal Chemistry*, 1994, 37(12), 1857-1864.
Sutton, S.C. et al., *Pharmaceutical Research*, 1993, 10(6), 924-926.
Suzuki et al., *Pain*, 2001, 91, 101-109.
Swahn, B.M. et al., *Bioorganic & Medicinal Chemistry Letters*, 1996, 6(14), 1635-1640.
Tang et al., *Nature*, 1999, 401, 63-69.
Wei et al., *Nature*, 2001, 4(2), 164-169.
Wilen, S.H. et al., *Tetrahedron*, 1977, 33, 2725-2736.
Woolf et al., *Pain*, 1991, 44, 293-299.
Yuan, L.C. et al., *Pharmaceutical Research*, 2001, 18(2), 234-237.
Zia, H. et al., *Clinical Research & Regulatory Affairs*, 1993, 10(2), 99-135.

DERIVATIVES OF [2-(8,9-DIOXO-2,6-DIAZABICYCLO[5.2.0]NON-1(7)-EN-2-YL)ALKYL] PHOSPHONIC ACID AND METHODS OF USE THEREOF

CROSS-REFERENCE TO RELATED APPLICATIONS

This application is a continuation of U.S. application Ser. No. 10/820,216, filed Apr. 7, 2004 (now allowed), which claims the benefit of U.S. Application No. 60/461,490, filed Apr. 9, 2003, the entire disclosures of which are incorporated herein by reference.

BACKGROUND OF THE INVENTION

The present invention relates to derivatives of [2-(8,9-dioxo-2,6-diazabicyclo[5.2.0]non-1(7)-en-2-yl)alkyl]phosphonic acid and methods of use thereof. The compounds of the present invention are particularly useful as N-methyl-D-aspartate (NMDA) receptor antagonists.

Glutamate and aspartate play dual roles in the central nervous system as essential amino acids and as the principal excitatory neurotransmitters. There are at least four classes of excitatory amino acid receptors: NMDA, AMPA (2-amino-3-(methyl-3-hydroxyisoxazol-4-yl)propanoic acid), kainate and metabotropic receptors. These excitatory amino acid receptors regulate a wide range of signaling events that impact physiological brain functions. For example, activation of the NMDA receptor has been shown to be the central event which leads to excitotoxicity and neuronal death in many disease states, as well as a result of hypoxia and ischaemia following head trauma, stroke and following cardiac arrest. It is also known that the NMDA receptor plays a major role in the synaptic plasticity that underlies many higher cognitive functions, such as memory and learning, certain nociceptive pathways, and in the perception of pain. In addition, certain properties of NMDA receptors suggest that they may be involved in the information-processing in the brain which underlies consciousness itself.

NMDA receptors are localized throughout the central nervous system. NMDA receptors are ligand-gated cation channels that modulate sodium, potassium and calcium ions flux when they are activated by glutamate in combination with glycine. Structurally, the NMDA receptor is thought to be comprised of heteromultimeric channels containing two major subunits designated as NR1 and NR2. These subunits contain a glycine binding site, a glutamate binding site and polyamine binding site. For the NR1 subunit, multiple splice variants have been identified, whereas for the NR2 subunit, four individual subunit types (NR2A, NR2B, NR2C, and NR2D) have been identified. The NMDA receptor also contains an $Mg^{++}$ binding site located inside the pore of the ionophore of the NMDA receptor/channel complex, which blocks the flow of ions.

Substantial preclinical and clinical evidence indicates that inhibitors of the N-methyl-D-aspartate (NMDA) receptor have therapeutic potential for treating numerous disorders. Disorders believed to be responsive to inhibition of NMDA receptors include cerebral vascular disorders such as cerebral ischemia (e.g., stroke) or cerebral infarction resulting in a range of conditions such as thromboembolic or hemorrhagic stroke, or cerebral vasospasm; cerebral trauma; muscular spasm; and convulsive disorders such as epilepsy or status epilepticus. NMDA receptor antagonists may also be used to prevent tolerance to opiate analgesia or to help control symptoms of withdrawal from addictive drugs.

Screening of compounds in recent years have identified a number of NMDA receptor antagonists that have been used in animal and clinical human studies to demonstrate proof of concept for the treatment of a variety of disorders. The difficulty with demonstrating clinical utility of NMDA receptor antagonists has generally been the antagonists' lack of NMDA receptor subtype selectivity and/or biological activity when dosed orally. Thus, the search for NMDA receptor antagonists that are subtype-selective and/or orally efficacious continues.

SUMMARY OF THE INVENTION

In one embodiment, the present invention provides compounds of formula (I) or a pharmaceutically acceptable salt thereof:

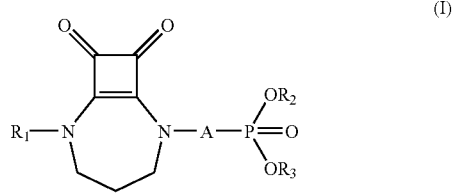

where:

$R_1$ is hydrogen, a $C_1$ to $C_6$ alkyl group, a $C_2$ to $C_7$ acyl group, a $C_1$ to $C_6$ alkanesulfonyl group, or a $C_6$ to $C_{14}$ aroyl group;

A is alkylene of 1 to 4 carbon atoms or alkenylene of 2 to 4 carbon atoms;

$R_2$ and $R_3$ are independently selected from hydrogen, or

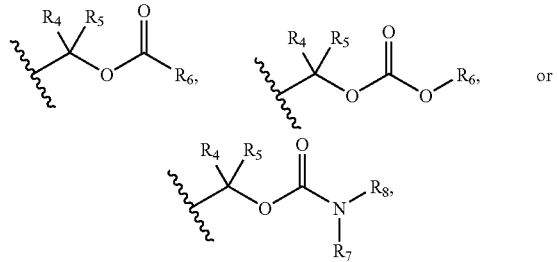

with the proviso that at least one of $R_2$ and $R_3$ is not hydrogen;

$R_4$ and $R_5$ are independently selected from hydrogen, a $C_1$ to $C_4$ alkyl group, a $C_5$ to $C_7$ aryl group, a $C_6$ to $C_{15}$ alkylaryl group having 5 to 7 carbon atoms in the aryl ring, a $C_2$ to $C_7$ alkenyl group, or $C_2$ to $C_7$ alkynyl group, or $R_4$ and $R_5$ may together form a spiro $C_3$ to $C_8$ carbocyclic ring;

$R_6$ is a $C_1$ to $C_{12}$ linear or branched alkyl group, a $C_2$ to $C_7$ linear or branched alkenyl or alkynyl group, a $C_5$ to $C_{13}$ aryl group, a $C_6$ to $C_{21}$ alkylaryl group having 5 to 13 carbon atoms in the aryl moiety; a 5 to 13 membered heteroaryl group, a 6 to 21 membered alkylheteroaryl group having 5 to 13 members in the heteroaryl moiety, a $C_4$ to $C_8$ cycloalkyl group, a $C_5$ to $C_{16}$ alkylcycloalkyl group having 4 to 8 carbon atoms in the cycloalkyl ring;

$R_7$ and $R_8$ are independently selected from hydrogen, a $C_1$ to $C_{12}$ linear or branched alkyl group, a $C_2$ to $C_7$ linear or branched alkenyl or alkynyl group, a $C_5$ to $C_{13}$ aryl group, a $C_6$ to $C_{21}$, alkylaryl group having 5 to 13 carbon atoms in the aryl moiety, a 5 to 13 membered heteroaryl group, a 6 to 21 membered alkylheteroaryl group having 5 to 13 members in the heteroaryl moiety, or $R_7$ and $R_8$ may together form a cycloalkyl or heterocycloalkyl group having in the ring 4 to 8 carbon atoms and optionally one to two atoms selected from nitrogen, oxygen or sulfur;

wherein any $R_1$ to $R_8$ group having an aryl, heteroaryl, cycloalkyl or heterocycloalkyl moiety may optionally be substituted on the aryl, heteroaryl, cycloalkyl or heterocycloalkyl moiety with 1 to about 5 substituents independently selected from a halogen atom, a cyano, nitro or hydroxyl group, a $C_1$-$C_6$ alkyl group, or a $C_1$-$C_6$ alkoxy group.

In another embodiment, the present invention provides a method for treating one or more conditions in a mammal that includes administering to a mammal in need thereof a therapeutically effective amount of a compound of formula (I) or a pharmaceutically acceptable salt thereof. Examples of conditions that may be treated in accordance with the methods of the present invention include cerebral vascular disorders such as cerebral ischemia or cerebral infarction; cerebral trauma; muscular spasm; convulsive disorders such as epilepsy or status epilepticus; glaucoma; pain; anxiety disorders; mood disorders; schizophrenia; schizophreniform disorder; schizoaffective disorder; cognitive impairment; chronic neurodegenerative disorders such as Parkinson's disease, Huntingdon's disease, Alzheimer's disease, amyotrophic lateral sclerosis, or chronic dementia; inflammatory diseases; hypoglycemia; diabetic end organ complications; cardiac arrest; asphyxia anoxia; spinal chord injury; fibromyalgia, complications from herpes zoster (shingles) such as prevention of post-herpetic neuralgia; prevention of tolerance to opiate analgesia; or withdrawal symptoms from addictive drugs or combinations thereof.

In another embodiment of the present invention, a pharmaceutical composition is provided that includes at least one compound of formula (I) and at least one pharmaceutically acceptable carrier.

In yet another embodiment of the present invention, a product is provided that is made by the process that includes reacting a compound of formula (II)

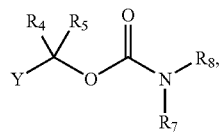

(II)

and at least one ester selected from

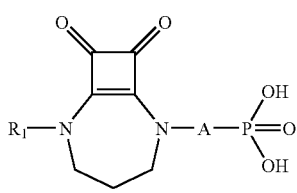

(i)

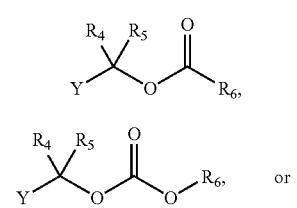

(ii)

-continued

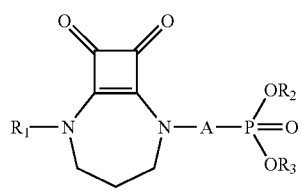

(iii)

and forming a product of formula (I) or a pharmaceutically acceptable salt thereof, where Y is a leaving group.

DETAILED DESCRIPTION OF THE INVENTION

This invention provides compounds of formula (I)

(I)

where:
$R_1$ is hydrogen, a $C_1$ to $C_6$ alkyl group, a $C_2$ to $C_7$ acyl group, a $C_1$ to $C_6$ alkanesulfonyl group, or a $C_6$ to $C_{14}$ aroyl group;

A is alkylene of 1 to 4 carbon atoms or alkenylene of 2 to 4 carbon atoms;

$R_2$ and $R_3$ are independently selected from hydrogen, or

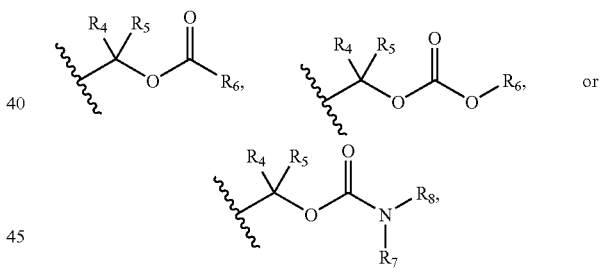

with the proviso that at least one of $R_2$ and $R_3$ is not hydrogen;

$R_4$ and $R_5$ are independently selected from hydrogen, a $C_1$ to $C_4$ alkyl group, a $C_5$ to $C_7$ aryl group, a $C_6$ to $C_{15}$ alkylaryl group having 5 to 7 carbon atoms in the aryl ring, a $C_2$ to $C_7$ alkenyl group, or $C_2$ to $C_7$ alkynyl group, or $R_4$ and $R_5$ may together form a spiro $C_3$ to $C_8$ carbocyclic ring;

$R_6$ is a $C_1$ to $C_{12}$ linear or branched alkyl group, a $C_2$ to $C_7$ linear or branched alkenyl or alkynyl group, a $C_5$ to $C_{13}$ aryl group, a $C_6$ to $C_{21}$, alkylaryl group having 5 to 13 carbon atoms in the aryl moiety; a 5 to 13 membered heteroaryl group, a 6 to 21 membered alkylheteroaryl group having 5 to 13 members in the heteroaryl moiety, a $C_4$ to $C_8$ cycloalkyl group, a $C_5$ to $C_{16}$ alkylcycloalkyl group having 4 to 8 carbon atoms in the cycloalkyl ring;

$R_7$ and $R_8$ are independently selected from hydrogen, a $C_1$ to $C_{12}$ linear or branched alkyl group, a $C_2$ to $C_7$ linear or branched alkenyl or alkynyl group, a $C_5$ to $C_{13}$ aryl group, a $C_6$ to $C_{21}$ alkylaryl group having 5 to 13 carbon atoms in the aryl moiety, a 5 to 13 membered heteroaryl group, a 6 to 21 membered alkylheteroaryl group having 5 to 13 members in the heteroaryl moiety, or $R_7$ and $R_8$ may together form a cycloalkyl or heterocycloalkyl group having in the ring 4 to 8 carbon atoms and optionally one to two atoms selected from nitrogen, oxygen or sulfur; or a pharmaceutically acceptable salt thereof.

Unless otherwise indicated:

Alkyl or alkylene as used herein, refers to an aliphatic hydrocarbon chain having 1 to 12 carbon atoms and includes, but is not limited to, straight or branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms. In some embodiments of the invention, alkyl is preferably $C_1$ to $C_8$ and more preferably $C_1$ to $C_6$.

Alkenyl or alkenylene refers to an aliphatic straight or branched hydrocarbon chain having 2 to 7 carbon atoms that may contain 1 to 3 double bonds. Examples of alkenylene for A are straight or branched mono-, di-, or polyunsaturated groups such as vinyl, prop-1-enyl, allyl, methallyl, but-1-enyl, but-2-enyl or but-3-enyl.

Alkynyl refers to an aliphatic, straight or branched, hydrocarbon chain having 2 to 7 carbon atoms that may contain 1 to 3 triple bonds.

Acyl, as used herein, refers to the group R—C(=O)— where R is an alkyl group of 1 to 6 carbon atoms. For example, a $C_2$ to $C_7$ acyl group refers to the group R—C(=O)— where R is an alkyl group of 1 to 6 carbon atoms.

Alkanesulfonyl, as used herein, refers to the group R—S(O)$_2$— where R is an alkyl group of 1 to 6 carbon atoms.

Aryl, as used herein, refers to an aromatic 5- to 13-membered mono- or bi-carbocyclic ring such as phenyl or napthyl. Preferably, groups containing aryl moieties are monocyclic having 5 to 7 carbon atoms in the ring. Heteroaryl means an aromatic 5- to 13-membered carbon containing mono- or bi-cyclic ring having one to five heteroatoms which independently may be nitrogen, oxygen or sulfur. Preferably, groups containing heteroaryl moieties are monocyclic having 5 to 7 members in the ring where one to two of the ring members are selected independently from nitrogen, oxygen or sulfur. Groups containing aryl or heteroaryl moieties may optionally be substituted as defined below or unsubstituted.

Aroyl, as used herein, refers to the group Ar—C(=O)— where Ar is aryl as defined above. For example, a $C_6$ to $C_{14}$ aroyl moiety refers to the group Ar—C(=O)— where Ar is an aromatic 5 to 13 membered carbocyclic ring.

Alkylaryl, as used herein refers to the group —R—Ar where Ar is aryl as defined above and R is an alkyl moiety having 1 to 8, preferably 1 to 6, and more preferably 1 to 4 carbon atoms. Examples of alkylaryl groups include benzyl, phenethyl, 3-phenylpropyl, and 4-phenyl butyl. Alkylheteroaryl, as used herein refers to the group —R-hetAr where hetAr is heteroaryl as defined above and R is an alkyl moiety having 1 to 8, preferably 1 to 6, and more preferably 1 to 4 carbon atoms.

Cycloalkyl, as used herein refers to a monocarbocyclic ring having 3 to 8 carbon atoms, e.g., cyclopropyl, cyclobutyl, cyclopentyl and cyclohexyl. Heterocycloalkyl refers to a carbon containing monocyclic ring having 3 to 8 ring members where one to two ring atoms are independently selected from nitrogen, oxygen or sulfur. Groups containing cycloalkyl or heterocycloalkyl moieties may optionally be substituted as defined below or unsubstituted.

Alkylcycloalkyl, as used herein, refers to the group —R-cycloalk where cycloalk is a cycloalkyl group as defined above and R is an alkyl moiety having 1 to 8, preferably 1 to 6, and more preferably 1 to 4 carbon atoms.

Halogen means fluorine, chlorine, bromine or iodine.

Substituted, as used herein, refers to a moiety, such as an aryl, heteroaryl, cycloalkyl or heterocycloalkyl moiety having from 1 to about 5 substituents, and more preferably from 1 to about 3 substituents independently selected from a halogen atom, a cyano, nitro or hydroxyl group, a $C_1$-$C_6$ alkyl group, or a $C_1$-$C_6$ alkoxy group. Preferred substituents are a halogen atom, a hydroxyl group, or a $C_1$-$C_6$ alkyl group.

In formula (I) above, in one embodiment of the present invention, $R_1$ is preferably H or a $C_1$ to $C_4$ alkyl group and more preferably H. In another embodiment of the present invention, A is preferably an alkylene group, —(CH$_2$)$_n$—, where n is 1 to 3, more preferably 1 to 2 and most preferably 2.

In another embodiment, $R_2$ and $R_3$ are preferably independently selected from H or:

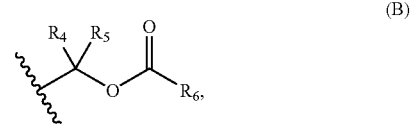
(B)

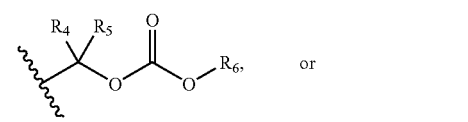
(C)

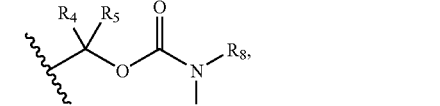
(D)

with the proviso that at least one of $R_2$ and $R_3$ is not H. When both $R_2$ and $R_3$ are not hydrogen, it is preferred that they be the same. $R_4$ and $R_5$ are preferably selected from H or a $C_1$ to $C_4$ alkyl group, and more preferably H or methyl. $R_6$ is preferably selected from a $C_3$ to $C_{10}$ linear or branched alkyl group, a $C_5$ to $C_7$ aryl group, a 5- to 7-membered heteroaryl group, or a cycloalkyl group having in the ring 5 to 7 carbon atoms. In a preferred embodiment $R_6$ is a $C_5$ to $C_7$ aryl group.

In another preferred embodiment of the present invention, $R_2$ and $R_3$ of formula (I) are H or the moiety (B) or (D),

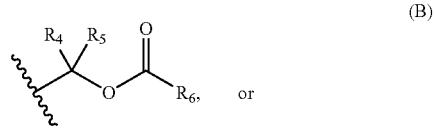
(B)

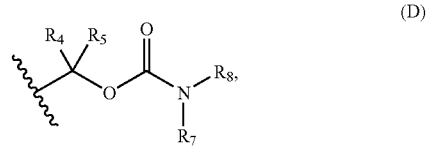
(D)

more preferably H or the moiety (B), and most preferably both are the moiety (B), where $R_4$, $R_5$ and $R_6$ are defined as above.

In yet another preferred embodiment of the present invention $R_1$ is H or a $C_1$ to $C_4$ alkyl group; A is an alkylene group having the formula —(CH$_2$)$_n$—, where n is 1 to 3; R$_2$ and R$_3$ are independently selected from H or:

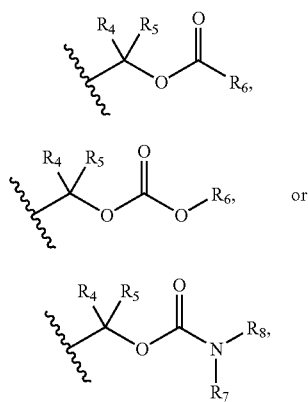

with the proviso that at least one of R$_2$ and R$_3$ is not H; R$_4$ and R$_5$ are independently selected from H or a C$_1$ to C$_4$ alkyl group; and R$_6$ is selected from a C$_3$ to C$_{10}$ linear or branched alkyl group, a C$_5$ to C$_7$ aryl group, a 5- to 7-membered heteroaryl group, or a cycloalkyl group having in the ring 5 to 7 carbon atoms.

In further embodiments, R$_6$ is selected from phenyl, n-hept-4-yl, cyclohexyl, isopropyl and t-butyl. In still further embodiments R$_7$ and R$_8$ are both methyl.

Specific examples of compounds of the present invention include the following compounds:
3-{2-[8,9-dioxo-2,6-diazabicyclo[5.2.0]non-1(7)-en-2-yl]ethyl}-3-oxido-7-oxo-7-phenyl-2,4,6-trioxa-3-phosphahept-1-yl benzoate;
3-{2-[8,9-dioxo-2,6-diazabicyclo[5.2.0]non-1(7)-en-2-yl]ethyl}-3-oxido-7-oxo-8-propyl-2,4,6-trioxa-3-phosphaundec-1-yl 2-propylpentanoate;
2,2-dimethyl-propionic acid (2,2-dimethyl-propionyloxymethoxy)-[2-(8,9-dioxo-2,6-diaza-bicyclo[5.2.0]non-1(7)-en-2-yl)-ethyl]-phosphinoyloxymethyl ester;
7-cyclohexyl-3-{2-[8,9-dioxo-2,6-diazabicyclo[5.2.0]non-1(7)-en-2-yl]ethyl}-1,5-dimethyl-3-oxido-7-oxo-2,4,6-trioxa-3-phosphahept-1-yl cyclohexanecarboxylate;
7-cyclohexyl-3-{2-[8,9-dioxo-2,6-diazabicyclo[5.2.0]non-1(7)-en-2-yl]ethyl}-3-oxido-7-oxo-2,4,6-trioxa-3-phosphahept-1-yl cyclohexanecarboxylate;
[2-(8,9-Dioxo-2,6-diaza-bicyclo[5.2.0]non-1-(7)-en-2-yl)-ethyl]-phosphonic acid diisopropoxycarbonyl oxymethyl ester;
[2-[8,9-dioxo-2,6-diazabicyclo[5.2.0]non-1(7)-en-2-yl]ethyl]-phosphonic acid bis[1-(benzoyloxy)ethyl]ester;
benzoic acid [2-(8,9-dioxo-2,6-diaza-bicyclo[5.2.0]non-1(7)-en-2-yl)-ethyl]-hydroxy-phosphinoyloxymethyl ester; and pharmaceutically acceptable salts thereof; and
[2-(8,9-Dioxo-2,6-diaza-bicyclo[5.2.0]non-1(7)-en-2-yl)-ethyl]-phosphonic acid di-dimethylcarbamoyloxymethyl ester; and
pharmaceutically acceptable salts thereof.

The compounds of this invention may contain asymmetric carbon atoms and/or phosphorus atoms, and thus can give rise to optical isomers and diastereoisomers. While shown without respect to stereochemistry in formula (I), the present invention includes such optical isomers and diastereoisomers; as well as the racemic and resolved, enantiomerically pure R and S stereoisomers; as well as other mixtures of the R and S stereoisomers and pharmaceutically acceptable salts thereof.

Where an enantiomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

One skilled in the art will also recognize that it is possible for tautomers to exist of formula (I). The present invention includes all such tautomers even though not shown in formula (I).

The compounds useful in the present invention also include pharmaceutically acceptable salts of the compounds of formula (I). By "pharmaceutically acceptable salt", it is meant any compound formed by the addition of a pharmaceutically acceptable base and a compound of formula (I) to form the corresponding salt. By the term "pharmaceutically acceptable" it is meant a substance that is acceptable for use in pharmaceutical applications from a toxicological perspective and does not adversely interact with the active ingredient. Preferably, the pharmaceutically acceptable salts are alkali metal (sodium, potassium, lithium) or alkaline earth metal (calcium, magnesium) salts of the compounds of formula (I), or salts of the compounds of formula (I) with pharmaceutically acceptable cations derived from ammonia or a basic amine. Examples of the later include, but are not limited to, ammonium, mono-, di-, or trimethylammonium, mono-, di-, or triethylammonium, mono-, di-, or tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 1-isopropylpyrrolidinium, 1,4-dimethylpiperazinium, 1-n-butylpiperidinium, 2-methylpiperidinium, 1-ethyl-2-methylpiperidinium, mono-, di-, or triethanolammonium, tris-(hydroxymethyl)methylammonium, or phenylmonoethanolammonium. Preferably, salts may be formed when one of R$_2$ or R$_3$ is hydrogen.

The compounds of the present invention can be prepared by synthesizing the compound of the formula (II), where A and R$_1$ are defined as for formula (I)

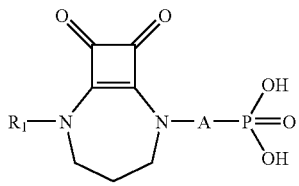

according to methods described in U.S. Pat. Nos. 5,168,103, 5,240,946, 5,990,307 and 6,011,168, the contents of which are entirely incorporated herein by reference. A preferred synthesis route is described in Example 5 of U.S. Pat. Nos. 5,990,307 and 6,011,168.

The compound of formula (II) obtained is then dissolved in a suitable solvent such as dimethylformamide. By "suitable solvent" it is meant a solvent that the compound of formula (II) is soluble in and nonreactive with. Preferably an acid scavenger (to react with the acid halide reaction by-product) such as an amine, is added to the reaction mixture at preferably ambient temperature. The amine is preferably a sterically hindered secondary or tertiary amine and more preferably a tertiary amine such as diisopropylethylamine. An appropriately substituted ester of the formula:

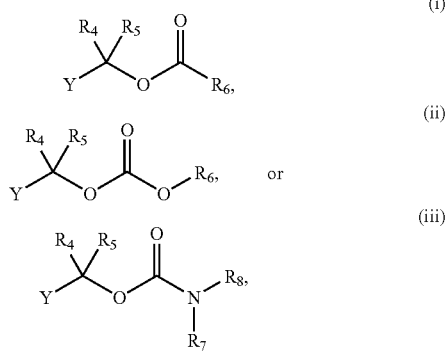

where $R_4$, $R_5$, and $R_6$ are defined as in formula (I), and Y is leaving group, is added to the reaction mixture. As used herein, the term "leaving group" refers to a moiety that can be selectively displaced by another moiety, such as by nucleophilic substitution or elimination, during a chemical reaction. Typically, leaving groups include moieties that when removed by nucleophilic substitution or elimination are relatively stable in anionic form. Leaving groups are well known in the art and include, for example, halides (e.g., chloride, bromide, and iodide) and alkyl- and arylsulfonates such as mesylate, tosylate, brosylate, nosylate, triflate, and the like. In a preferred embodiment, Y is a halogen atom.

The reaction mixture is heated from about 50° C. to about 80° C., and more preferably from about 65° C. to about 75° C. for a sufficient reaction time so that the halo ester reacts with the compound of formula (II) to form a compound of formula (I). Typically, for preferable yields, the reaction time is from about 20 hours to about 40 hours, and more preferably from about 25 hours to about 35 hours. After the reaction is complete, the reaction mixture is preferably cooled to ambient temperature, and the compound of formula (I) is isolated using standard techniques known to those skilled in the art. A preferred isolation method is to partition the reaction mixture between a mild base, such as aqueous sodium bicarbonate, and an organic solvent such as ethyl acetate. The aqueous phase is preferably several times re-extracted with the organic solvent, and the combined organic layers are washed again with a mild base. The organic layers are then dried, for example with brine and over magnesium sulfate, filtered and evaporated. The residue is then preferably flash chromatographed on silica gel using standard techniques to isolate the compound.

The compounds of the present invention, when administered to mammals, are NMDA antagonists, and are thus useful for treating a variety of disorders that benefit from inhibiting the NMDA receptor in mammals. By "treating", as used herein, it is meant partially or completely alleviating, inhibiting, preventing, ameliorating and/or relieving the disorder. For example, "treating" as used herein includes partially or completely alleviating, inhibiting or relieving the condition in question. "Mammals" as used herein refers to warm blooded vertebrate animals, such as humans.

Accordingly, the present invention provides methods for treating conditions in mammals that would benefit from inhibiting the NMDA receptor that includes administering to a mammal in need thereof a therapeutically effective amount of at least one compound of formula (I).

While in no way intending to be bound in theory, it is believed that the compounds of the present invention after administration into a mammal, form the corresponding phosphonic acid (i.e., where R2 and/or R3 are hydrogen in formula (I)). It has surprisingly been discovered that compounds of the present invention relative to compounds of formula (II) have improved bioavailability when administered orally to mammals. Additionally, the compounds of the present invention, after administration into mammals, have a unique affinity and selectivity for certain binding sites on the NMDA receptor. This unique affinity and selectivity is believed to provide effective treatment at lower doses and/or cause less side effects at doses to provide the desired treatment. This is particularly evident when the condition being treated is pain.

In one embodiment, the present invention provides methods for treating conditions associated with glutamate abnormalities that includes administering to a mammal in need thereof a therapeutically effective amount of at least one compound of formula (I). As used herein, "associated with" refers to conditions directly or indirectly caused by glutamate abnormalities. "Glutamate abnormality" refers to any condition produced by a disease or a disorder in which glutamate, typically in increased amounts, is implicated as a contributing factor to the disease or disorder. Conditions believed to be associated with glutamate abnormality include, but are not limited to, cerebral vascular disorders such as cerebral ischemia (e.g., stroke) or cerebral infarction resulting in a range of conditions such as thromboembolic or hemorrhagic stroke, or cerebral vasospasm; cerebral trauma; muscular spasm; convulsive disorders such as epilepsy or status epilepticus; glaucoma; pain; anxiety disorders such as such as panic attack, agoraphobia, panic disorder, specific phobia, social phobia, obsessive compulsive disorder, posttraumatic stress disorder, acute stress disorder, generalized anxiety disorder, separation anxiety disorder, or substance-induced anxiety disorder; mood disorders such as bipolar disorders (e.g., bipolar I disorder, bipolar II disorder, and cyclothymic disorder), depressive disorders (e.g., major depressive disorder, dysthymic disorder, or substance-induced mood disorder), mood episodes (e.g., major depressive episode, manic episode, mixed episode, and hypomanic episode); schizophrenia; schizophreniform disorder; schizoaffective disorder; cognitive impairment such as memory loss; and chronic neurodegenerative disorders such as Parkinson's disease, Huntingdon's disease, Alzheimer's disease, amyotrophic lateral sclerosis, or chronic dementia related to, for example, Lewy body disease, Alzheimer's disease, fronto temporal, or AIDS. With respect to the mental disorders listed above such as schizophrenia, mood disorders and anxiety disorders, reference is made to the Diagnostic and Statistical Manual of Mental Disorders, 4$^{th}$ edition, Washington, D.C., American Psychiatric Association (1994) for a more complete description of each of the mental disorder. Additional conditions believed to be related to glutamate abnormalities include inflammatory diseases; hypoglycemia; diabetic end organ complications; cardiac arrest; asphyxia anoxia, such as from near drowning, pulmonary surgery and cerebral trauma; and spinal chord injury. The compounds of the present invention may also be used to treat fibromyalgia, and complications from herpes zoster (shingles) such as prevention of postherpetic neuralgia. Thus, the present invention provides methods for treating each of the aforementioned conditions or combinations of these conditions that includes administering to a mammal in need thereof a therapeutically effective amount of at least one compound of formula (I).

In one preferred embodiment, the compounds of the present invention are used to treat pain. The pain may be, for example, acute pain (short duration) or chronic pain (regularly reoccurring or persistent). The pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain or dental pain, or headaches such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromylagia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, herpes zoster (shingles), sickle cell anemia, autoimmune disorders, multiple sclerosis, or inflammation such as osteoarthritis or rheumatoid arthritis.

In a more preferred embodiment, the compounds useful in this invention are used to treat chronic pain that is neuropathic pain, visceral pain, musculoskeletal pain, bony pain, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. The methods of use for compounds of this invention further include treatments in which the neuropathic pain is a condition secondary to metastatic infiltration, adiposis dolorosa, burns or central pain conditions related to thalamic conditions.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention may also be used to treat acute and/or chronic pains associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

The compounds of the present invention may also be used to prevent tolerance to opiate analgesia or to help control symptoms of withdrawal from addictive drugs.

The compounds of the present invention can be administered in any way known to those skilled in the art, including for example, by oral or parenteral administration such as by intramuscular, intraperitoneal, epidural, intrathecal, intravenous, subcutaneous, intramucosal such as sublingual or intranasal, vaginal, rectal or transdermal administration. In a preferred embodiment of the present invention, the compounds of the present invention are administered orally, intramucosally or intravenously. With respect to intranasal administration, reference is made to copending provisional application Ser. No. 60/461,571, filed on Apr. 9, 2003 and U.S. application Ser. No. not yet assigned, filed concurrently herewith, and entitled "Pharmaceutical Compositions For Intranasal Administration Of [2-(8,9-Dioxo-2,6-Diazabicyclo[5.2.0] Non-1(7)-En-2-Yl)Alkyl]Phosphonic Acid And Derivatives And Methods Of Use Thereof," the disclosures of which are hereby incorporated by reference in their entireties.

The compounds of the present invention are administered in a therapeutically effective amount to the mammal needing treatment. As used herein "a therapeutically effective amount" is at least the minimal amount of the compound or a pharmaceutically acceptable salt form thereof, which treats the condition in question in a mammal. The therapeutically effective amount will depend on such variables as the particular composition used, the route of administration, the severity of the symptoms, and the particular patient being treated. To determine the therapeutically effective amount of the compound to be administered, the physician may, for example, evaluate the effects of a given compound of formula (I) in the patient by incrementally increasing the dosage until the desired symptomatic relief level is achieved. The continuing dose regimen may then be modified to achieve the desired result. For example, in the case of an oral dosage, preferably the compounds of the present invention are incrementally increased in a patient in an amount of from 3 mg/kg to 1000 mg/kg until the desired symptomatic relief level is achieved. The continuing dose regimen may then be modified to achieve the desired result, with the range for oral dosage being preferably from about 20 mg/day to about 900 mg/day. Similar techniques may be followed by determining the effective dose range for other administration routes such as by intravenous or intramuscular routes based on bioavailability data.

In another embodiment of the present invention, the compounds of the present invention may be administered to a mammal with one or more other pharmaceutical active agents such as those agents being used to treat any other medical condition present in the mammal. Examples of such pharmaceutical active agents include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), and/or successively with one or more compounds of the present invention.

The method of administration of the other pharmaceutical active agent may be the same or different from the route of administration used for the compounds of the present invention. For example, the other pharmaceutical active agents may be administered by oral or parental administration, such as for example, by intramuscular, intraperitoneal, epidural, intrathecal, intravenous, intramucosal such as by intranasal or sublingual, subcutaneous or transdermal administration. The preferred administration route will depend upon the particular pharmaceutical active agent chosen and its recommended administration route(s) known to those skilled in the art.

A more complete listing of pharmaceutical active agent can be found in the Physicians' Desk Reference, 55 Edition, 2001, published by Medical Economics Co., Inc., Montvale, N.J. Each of these agents may be administered according to the therapeutically effective dosages and regimens known in the art, such as those described for the products in the Physicians' Desk Reference, 55 Edition, 2001, published by Medical Economics Co., Inc., Montvale, N.J.

In a preferred embodiment of the present invention, the compounds of the present invention may be administered to a mammal with one or more other pain relieving agents to treat pain in a mammal. By "pain relieving agents" it is meant any agent that directly or indirectly treats pain symptoms. Examples of indirect pain relieving agents include for example anti-inflammatory agents, such as anti-rheumatoid agents.

The one or more other pain relieving agents may be administered simultaneously (such as individually at the same time, or together in a pharmaceutical composition), and/or successively with the compounds of the present invention. Preferably, the compounds of the present invention and the one or more pain relieving agents are administered in a manner so that both are present in the mammal body for a certain period of time to treat pain.

The method of administration of the other pain relieving agent may be the same or different from the route of administration used for the compound of the present invention. For example, opioids are preferably administered by oral, intravenous, or intramuscular administration routes.

One skilled in the art will recognize that the dosage of the other pain relieving agent administered to the mammal will depend on the particular pain relieving agent in question and the desired administration route. Accordingly, the other pain relieving agent may be dosed and administered according to those practices known to those skilled in the art such as those disclosed in references such as the Physicians' Desk Reference, 55 Edition, 2001, published by Medical Economics Co., Inc., Montvale, N.J.

Examples of pain relieving agents that may be administered with the compound of the present invention include analgesics such as non-narcotic analgesics or narcotic analgesics; anti-inflammatory agents such as non-steroidal anti-inflammatory agents (NSAID), steroids or anti-rheumatic agents; migraine preparations such as beta adrenergic blocking agents, ergot derivatives, or isometheptene; tricyclic anti-depressants such as amitryptyline, desipramine, or imipramine; anti-epileptics such as gabapentin, carbamazepine, topiramate, sodium valproate or phenytoin; $\alpha_2$ agonists; or selective serotonin reuptake inhibitors/selective norepinepherine uptake inhibitors, or combinations thereof. One skilled in the art will recognize that some agents described hereinafter act to relieve multiple conditions such as pain and inflammation, while other agents may just relieve one symptom such as pain. A specific example of an agent having multiple properties is aspirin, where aspirin is anti-inflammatory when given in high doses, but at lower doses is just an analgesic. The pain relieving agent may include any combination of the aforementioned agents, for example, the pain relieving agent may be a non-narcotic analgesic in combination with a narcotic analgesic.

Non-narcotic analgesics useful in the present invention include, for example, salicylates such as aspirin, ibuprofen (MOTRIN®, ADVIL®), ketoprofen (ORUDIS®), naproxen (NAPROSYN®), acetaminophen, indomethacin or combinations thereof. Examples of narcotic analgesic agents that may be used in combination with the cyclobutene derivatives include opioid analgesics such as fentenyl, sufentanil, morphine, hydromorphone, codeine, oxycodone, buprenorphine or pharmaceutically acceptable salts thereof or combinations thereof. Examples of anti-inflammatory agents that may be used in combination with the cyclobutene derivatives include but are not limited to aspirin; ibuprofen; ketoprofen; naproxen; etodolac (LODINE®); COX-2 inhibitors such as celecoxib (CELEBREX®), rofecoxib (VIOXX®), valdecoxib (BEXTRA®), parecoxib, etoricoxib (MK663), deracoxib, 2-(4-ethoxy-phenyl)-3-(4-methanesulfonyl-phenyl)-pyrazolo[1,5-b]pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-Methylsulfonyl-4-(1,1-dimethyl-4-(4-fluorophenyl)cyclopenta-2,4-dien-3-yl)benzene, 4-(1,5-Dihydro-6-fluoro-7-methoxy-3-(trifluoromethyl)-(2)-benzothiopyrano(4,3-c)pyrazol-1-yl) benzenesulfonamide, 4,4-dimethyl-2-phenyl-3-(4-methylsulfonyl)phenyl)cyclo-butenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, or their physiologically acceptable salts, esters or solvates; sulindac (CLINORIL®); diclofenac (VOLTAREN®); piroxicam (FELDENE®); diflunisal (DOLOBID®), nabumetone (RELAFEN®), oxaprozin (DAYPRO®), indomethacin (INDOCIN®); or steroids such as PEDIAPED® prednisolone sodium phosphate oral solution, SOLU-MEDROL® methyiprednisolone sodium succinate for injection, PRELONE® brand prednisolone syrup.

Further examples of anti-inflammatory agents preferably used for treating rheumatoid arthritis include naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDIINE EN-tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, or ENBREL® etanerecept products.

Examples of other agents used to treat inflammations, especially rheumatoid arthritis include immunosuppressants such as GENGRAF™ brand cyclosporine capsules, NEORAL® brand cyclosporine capsules or oral solution, or IMURAN® brand azathioprine tablets or IV injection; INDOCIN® brand indomethacin capsules, oral suspension or suppositories; PLAQUENIL® brand hydroxychloroquine sulfate; or REMICADE® infliximab recombinant for IV injection; or gold compounds such as auranofin or MYOCHRISYINE® gold sodium thiomalate injection.

In a preferred embodiment of the present invention, at least one compound of the present invention is administered with at least one opioid analgesic in accordance with the methods previously described herein to treat pain. It has been found that the compounds of the present invention, when administered with at least one opioid analgesic such as morphine, have such beneficial effects as synergisticaily decreasing pain perception, increasing the duration of pain relief, and/or decreasing adverse side effects.

The compounds of the present invention may be administered neat (i.e., as is) or in a pharmaceutical composition containing at least one pharmaceutically acceptable carrier. Thus, the present invention also provides pharmaceutical compositions containing a pharmaceutically effective amount of at least one compound of formula (I) or pharmaceutically acceptable salt thereof, and at least one pharmaceutically acceptable carrier. Preferred compounds to be present in the pharmaceutical compositions of the present invention include those compounds of formula (I) previously described as being preferred. Pharmaceutically acceptable carriers are those that are compatible with the other ingredients in the formulation and biologically acceptable. The pharmaceutical compositions may be administered to a mammal to treat a variety of conditions that would benefit from inhibiting the NMDA receptor as previously described herein.

Pharmaceutical compositions useful in the present invention may be in any form known to those skilled in the art such as in liquid or solid form. The proportion of ingredients will depend on such factors as the solubility and chemical nature of the compound of formula (I) and the chosen route of administration. Such compositions are prepared in accordance with acceptable pharmaceutical procedures, such as described in Remingtons Pharmaceutical Sciences, 17th edition, ed. Alfonoso R. Gennaro, Mack Publishing Company, Easton, Pa. (1985).

Pharmaceutical compositions, in addition to containing a therapeutically effective amount of one or more compounds of the present invention and a pharmaceutically acceptable carrier may include one or more other ingredients known to those skilled in the art for formulating pharmaceutical compositions. Such ingredients include for example, flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators, or combinations thereof.

Solid pharmaceutical compositions preferably contain one or more solid carriers, and optionally one or more other additives such as flavoring agents, lubricants, solubilizers, suspending agents, fillers, glidants, compression aids, binders or tablet-disintegrating agents or an encapsulating material. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes or ion exchange resins, or combinations thereof. In powder pharmaceutical compositions, the carrier is preferably a finely divided solid which is in admixture with the finely divided active ingredient. In tablets, the active ingredient is mixed with a carrier having the necessary compression properties in suitable proportions, and optionally, other additives, and compacted into the desired shape and size. Solid pharmaceutical compositions, such as powders and tablets, preferably contain up to 99% of the active ingredient.

Liquid pharmaceutical compositions preferably contain one or more compounds of the present invention and one or more liquid carriers to form for example solutions, suspensions, emulsions, syrups, elixirs, or pressurized compositions. Pharmaceutically acceptable liquid carriers include for example water, organic solvent, pharmaceutically acceptable oils or fat, or combinations thereof. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators, or combinations thereof.

Examples of liquid carriers suitable for oral or parenteral administration include water (preferably containing additives such as cellulose derivatives such as sodium carboxymethyl cellulose), alcohols or their derivatives (including monohydric alcohols or polyhydric alcohols such as glycols) or oils (e.g., fractionated coconut oil and arachis oil). For parenteral administration the carrier can also be an oily ester such as ethyl oleate and isopropyl myristate. The liquid carrier for pressurized compositions can be halogenated hydrocarbons or other pharmaceutically acceptable propellant.

Liquid pharmaceutical compositions which are sterile solutions or suspensions can be administered parenterally, for example by, intramuscular, intraperitoneal, epidural, intrathecal, intravenous or subcutaneous injection. Pharmaceutical compositions for oral or transmucosal administration may be either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

In another embodiment of the present invention, the pharmaceutical composition, in addition to containing a compound of the present invention may also contain a therapeutically effective amount of one or more pain relieving agents as previously described herein, and/or a therapeutically effective amount one or more other pharmaceutical active agents as previously described herein. Thus, the present invention also provides a pharmaceutical composition containing a therapeutically effective amount of at least one compound of the present invention and a therapeutically effective amount of at least one pharmaceutical active agent, such as a pain relieving agent as previously described. For example, the pharmaceutical composition may contain one or more pain relieving agents that includes an opioid analgesic.

Preferably, the pharmaceutical composition is in unit dosage form, such as tablets or capsules. In such form, the composition is sub-divided in unit dose containing appropriate quantities of the active ingredient. The unit dosage forms can be packaged compositions, for example packeted powders, vials, ampoules, pre-filled syringes or sachets containing liquids. The unit dosage form can be, for example, a capsule or tablet itself, or it can be the appropriate number of any such compositions in package form.

Thus, the present invention also provides a pharmaceutical composition in unit dosage form that contains a therapeutically effective unit dosage of at least one compound of the present invention. As one skilled in the art will recognize, the preferred unit dosage will depend on for example the method of administration and the condition being treated. For example, a unit dosage for oral administration for treating pain preferably ranges from about 20 mg to about 300 mg of the compound of the present invention.

The present invention also provides a therapeutic package for dispensing the compound of the present invention to a mammal being treated. Preferably, the therapeutic package contains one or more unit dosages of the compound of the present invention and a container containing the one or more unit dosages and labeling directing the use of the package for treating the condition, such as pain, in a mammal. In a preferred embodiment, the unit dose is in tablet or capsule form. In a preferred embodiment, each unit dosage is in a therapeutically effective amount for treating pain.

EXAMPLES

Compounds of the present invention were prepared and evaluated for their ability to treat pain. In the synthesis of Examples of 1 through 10, the starting material [2-(8,9-dioxo-2,6-diazabicyclo[5.2.0]non-1(7)-en-2-yl)ethyl]phosphonic acid was prepared according to the procedure described in U.S. Pat. No. 5,990,307, Example No. 5. All other chemicals and intermediates used in the examples are either commercially available, can be prepared by standard procedures found in the literature, or are described in the examples.

Example 1

3-{2-[8,9-Dioxo-2,6-diazabicyclo[5.2.0]non-1(7)-en-2-yl]ethyl}-3-oxido-7-oxo-7-phenyl-2,4,6-trioxa-3-phosphahept-1-yl benzoate A solution of [2-(8,9-dioxo-2,6-diazabicyclo[5.2.0]non-1(7)-en-2-yl)ethyl]phosphonic acid (20.16 mmol, 5.25 g) in dry DMF (120 mL) was treated with N,N-diisopropylethylamine (80.64 mmol, 14 ml) for ½ hour at ambient temperature. Benzoic acid chloromethyl ester (60.49 mmol, 10.32 g, synthesis described below) was added at ambient temperature under exclusion of moisture. The reaction mixture was heated to 65° C. for 20 hours. The temperature was then raised to 72° C. and stirred at 72° C. for 16 hours after which the reaction was completed. The mixture was cooled to room temperature and partitioned between 10% sodium bicarbonate and ethyl acetate. After separation of the layers the aqueous phase was again extracted with ethyl acetate (6×) until there was no more product in the water phase (by silica gel TLC, 7% 2M ammonia in methanol and 93% chloroform). The combined organic layers were washed with brine, dried over magnesium sulfate, filtered and evaporated to dryness. The residue was flash chromatographed on 400 g silica gel using a solvent mixture of 1% 2M ammonia in methanol and 99% chloroform. Gradually the percentage of ammonia in methanol was increased to 7% and 93% chloroform. The solvent was evaporated in vacuo to yield the desired product (10.5 g, 99%; glass like material). MS (ES−): m/e 527 (M−H).

Preparation of Reactant Benzoic Acid Chloromethyl Ester

Para-formaldehyde (4.5 g) and zinc chloride (catalytic amount) were mixed together at 0° C. Benzoyl chloride (0.142 mole, 20 g) was added dropwise over 1 hour. The reaction was warmed to ambient temperature, then was heated to 55° C. for 10 hours. The progress of the reaction was followed by TLC (silica gel, 5/95, ethyl acetate/hexane). Since the starting material was still seen, an additional 1 g para-formaldehyde was added. The reaction was continued stirring at 55° C. for an additional 10 hours, cooled and flash chromatographed on 500 g silica gel, eluting with a solvent mixture of 2% ethyl acetate and 98% hexane. The solvent was evaporated in vacuo. Since the product had a low boiling point, the rotovapor bath temperature was not above 35° C. The desired product, 11.82 g (49%) was obtained as clear oil. MS (ES+): m/e 171 (M+H).

Example 2

3-{2-[8,9-Dioxo-2,6-diazabicyclo[5.2.0]non-1(7)-en-2-yl]ethyl}-3-oxido-7-oxo-8-propyl-2,4,6-trioxa-3-Phosphaundec-1-yl 2-propylpentanoate A solution of the starting [2-(8,9-dioxo-2,6-diazabicyclo[5.2.0]non-1(7)-en-2-yl)ethyl]phosphonic acid (26 mmol, 6.765 g) in dry DMF (250 mL) was treated with N,N-diisopropylethylamine (104 mmol, 13.442 g) followed by 2-propyl-pentanoic acid chloromethyl ester (88 mmol, 17 g, synthesis described below) at ambient temperature and under exclusion of moisture. The reaction mixture was heated to 65° C. and held, with stirring, at 65° C. for over 16 hours. The solvent was removed by vacuum distillation and the residue was partitioned (2×) between water and ether. The organic phase was separated, dried over magnesium sulfate, filtered, and evaporated to dryness affording about 16 g of crude product as a dense yellow oil. This oil was flash chromatographed on 350 g silica gel. Elution with 8% methanol/ethyl acetate afforded 8.4 g (56%) of the desired product as a colorless solidified wax. MS (ES+): m/e 573 (M+H).

Preparation of Reactant 2-propyl-pentanoic Acid Chloromethyl Ester

Para-formaldehyde (1 g) and zinc chloride (catalytic amount) were mixed together at 0° C. 2,2-Di-n-propylacetyl chloride (30 mole, 4.88 g) was added dropwise over 1 hour. The reaction was warmed to ambient temperature, then was heated to 50-55° C. for 6 hours. The reaction mixture continued stirring at room temperature for 16 hours. The reaction mixture was taken up with methylene chloride (5 mL) and flash chromatographed on 150 g silica gel. Elution with 1 to 5% ethyl acetate/hexane gave 3.3 g (58%) of the desired product.

Example 3

2,2-Dimethyl-propionic acid (2,2-dimethyl-propionyloxymethoxy)-[2-(8,9-dioxo-2,6-diaza-bicyclo [5.2.0]non-1(7)-en-2-yl)-ethyl]-phosphinoyloxymethyl ester A solution of the starting [2-(8,9-dioxo-2,6-diazabicyclo [5.2.0]non-1(7)-en-2-yl)ethyl]phosphonic acid (20 mmol, 5.2 g) in dry DMF (60 mL) was treated with N,N-diisopropylethylamine (80 mmol, 10.34 g) followed by commercially obtained chloromethyl pivalate (66 mmol, 9.94 g) at ambient temperature and under exclusion of moisture. The reaction mixture was heated to 65° C. and held, with stirring, at 65° C. for over 24 hours. The solvent was removed by vacuum distillation and the residue was partitioned (2×) between water and toluene. The organic phase was separated, dried over magnesium sulfate, filtered, and evaporated to dryness affording some 14 g of crude product as a dense amber oil. This oil was flash chromatographed on 400 g silica gel. Elution with 6% methanol/ethyl acetate afforded 5.88 g (60.2%) of the desired product. MS (ES+): m/e 489 (M+H).

Examples 4 to 5

Stereoisomers of 7-Cyclohexyl-3-{2-[8,9-dioxo-2,6-diazabicyclo[5.2.0]non-1(7)-en-2-yl]ethyl}-1,5-dimethyl-3-oxido-7-oxo-2,4,6-trioxa-3-phosphahept-1-yl cyclohexanecarboxylate A solution of the starting [2-(8,9-dioxo-2,6-diazabicyclo [5.2.0]non-1(7)-en-2-yl)ethyl]phosphonic acid (10 mmol, 2.6 g) in dry DMF (30 mL) was treated with N,N-diisopropylethylamine (33 mmol, 4.3 g) followed by cyclohexanecarboxylic acid 1-chloro-ethylester (33 mmol, 6.293 g) at ambient temperature and under exclusion of moisture. The reaction mixture was heated to 65° C. and held with stirring at 65° C. for over 24 hours. The solvent was removed by vacuum distillation and the residue was partitioned (2×) between water and toluene. The organic phase was separated, dried over magnesium sulfate, filtered, and evaporated to dryness affording some 7 g of crude product as a dense oil. This oil was flash chromatographed on 250 g silica gel. Elution with 3% methanol/ethyl acetate afforded 0.95 g (17%) of Example 4. MS (ES−): m/e 567 (M−H). A less polar diastereomer of 7-cyclohexyl-3-{2-[8,9-dioxo-2,6-diazabicyclo[5.2.0]non-1 (7)-en-2-yl]ethyl}-1,5-dimethyl-3-oxido-7-oxo-2,4,6-trioxa-3-phosphahept-1-yl cyclohexanecarboxylate (Example 5) was eluted to give upon evaporation in vacuo 0.35 g (6%) of Example 5. MS (ES−): m/e 567 (M−H).

Example 6

7-Cyclohexyl-3-{2-[8,9-dioxo-2,6-diazabicyclo [5.2.0]non-1(7)-en-2-yl]ethyl}-3-oxido-7-oxo-2,4,6-trioxa-3-phosphahept-1-yl cyclohexanecarboxylate A solution of the starting [2-(8,9-dioxo-2,6-diazabicyclo [5.2.0]non-1(7)-en-2-yl)ethyl]phosphonic acid (8.17 mmol, 2.1 g) in dry DMF (50 mL) was treated with N,N-diisopropylethylamine (33.34 mmol, 5.7 mL). After 30 minutes stirring at ambient temperature chloromethyl cyclohexanecarboxylate (4.33 g, 8.17 mmole) was added at ambient temperature and under exclusion of moisture. The reaction mixture was heated to 72° C. and held, with stirring, at 72° C. for over 36 hours. After cooling the mixture to room temperature aqueous sodium bicarbonate (10%, 50 mL) was added and the product was extracted with ethyl acetate (5× with 50 mL). The combined organic layers were washed with brine, dried over magnesium sulfate, filtered and evaporated in vacuo. The obtained residue was flash chromatographed on 200 g silica gel. Elution with a gradient of 1 to 5% methanol/ethyl acetate afforded 3.2 g (73%) of Example 6. The product was crystallized from ethyl acetate:ether:hexane, 70:15:15 to give 2.75 g of the desired product as an off-white microcrystalline solid melting at 64-65° C. MS (ES+): m/e 541 (M+H).

Example 7

[2-(8,9-Dioxo-2,6-diaza-bicyclo[5.2.0]non-1-(7)-en-2-yl)-ethyl]-phosphonic acid diiso propoxycarbonyloxymethyl ester A solution of the starting [2-(8,9-dioxo-2,6-diazabicyclo [5.2.0]non-1(7)-en-2-yl)ethyl]phosphonic acid (9.61 mmol, 2.5 g) in dry DMF (40 mL) was treated at once with N,N-diisopropylethylamine (33.62 mmol, 5.86 mL). The reaction mixture was stirred for 30 minutes at ambient temperature after which carbonic acid chloromethyl ester isopropyl ester (28.82 mmole, 4.4 g, synthesis described below) was added. Under stirring the mixture was heated to 70° C. for 24 hours. Thereafter the mixture was cooled to ambient temperature, citric acid (2% aqueous solution, 40 mL) added. The product was extracted with ethyl acetate (2×40 mL) followed by another extraction with chloroform (2×40 mL). The combined organic layers were dried over magnesium sulfate, filtered, and the filtrate evaporated to dryness. The residue was flash chromatographed on silica gel. Elution with a gradient of 2 to 7% ammonia in chloroform followed by a crystallization from ethyl acetate/ether/hexane afforded 2.1 g (44.4%) of the product as an off-white solid melting at 74-75° C. MS (ES+): m/e 493 (M+H).

Preparation of Reactant Carbonic Acid Chloromethyl Ester Isopropyl Ester

2-Propanol (73.14 mmole, 5.6 mL) was added to a solution of chloromethyl chloroformate (73.85 mmole, 6.5 mL) in ether (100 mL). The reaction mixture was cooled to 0° C. and pyridine (74.18 mmole, 6 mL) was dropwise added with stirring. Thereafter, the reaction mixture was stirred at ambient temperature for 20 hours. The formed solids were filtered and the filtrate was washed with citric acid (1% aqueous), water, sodium bicarbonate solution (1%) and brine. The organic layer was dried over magnesium sulfate, filtered, and evaporated to dryness to yield 10.26 g (92%) of a colorless oil. MS (ES+): m/e 152 (M+H).

Examples 8 to 9

Stereoisomers of [2-[8,9-Dioxo-2,6-diazabicyclo [5.2.0]non-1(7)-en-2-yl]ethyl]-Phosphonic acid bis [1-(benzoyloxy)ethyl]ester A solution of the starting [2-(8,9-dioxo-2,6-diazabicyclo [5.2.0]non-1(7)-en-2-yl)ethyl]phosphonic acid (19.22 mmol, 5 g) in dry DMF (100 mL) was treated with N,N-diisopropylethylamine (76.88 mmol, 13.39 mL). The reaction mixture was stirred for 30 minutes at ambient temperature after which benzoic acid-1-chloroethyl ester (57.66 mmole, 10.65 g, synthesis described below) was added. The mixture was then stirred at 70° C. for 36 hours, cooled to ambient temperature and diluted with citric acid (2% aqueous solution, 70 mL). The product was extracted with ethyl acetate (3×50 mL), washed with sodium bicarbonate (3%) and brine. The organic layer was dried over magnesium sulfate, filtered, and evaporated to dryness. The residue was flash chromatographed on silica gel. Elution with a gradient of 2 to 8% methanol in chloroform afforded 1.66 g (15.5%) of a stereoisomer of [2-[8,9-Dioxo-2,6-diazabicyclo[5.2.0]non-1(7)-en-2-yl] ethyl]-phosphonic acid bis[1-(benzoyloxy)ethyl]ester (example 8) [MS (ES+): m/e 557 (M+H)] and 0.73 g (6.8%) of a less polar diastereoisomer of [2-[8,9-Dioxo-2,6-diazabicyclo [5.2.0]non-1(7)-en-2-yl]ethyl]-phosphonic acid bis[1-(benzoyloxy)ethyl]ester (example 9) [MS (ES+): m/e 557 (M+H)].

Preparation of Reactant Benzoic acid-1-chloroethyl Ester

A mixture of benzoyl chloride (177.85 mmole, 20.63 mL) and zinc chloride (0.2 g) was cooled to −20° C. Acetaldehyde (178.88 mmole, 10 mL) was added dropwise and the reaction mixture stirred at −20° C. for 1 hour then warmed to ambient temperature and stirring continued for 18 hours. The whole mixture was flash chromatographed on silica gel. Elution with a gradient of 2 to 7% ethyl acetate in hexane afforded 22.43 g (68%) of the product as a colorless oil. MS (ES+): m/e 171 (M+H).

Example 10

Benzoic acid [2-(8,9-dioxo-2,6-diaza-bicyclo[5.2.0] non-1(7)-en-2-yl)-ethyl]-hydroxy-phosphinoyloxymethyl ester A solution of 3-{2-[8,9-dioxo-2,6-diazabicyclo[5.2.0] non-1(7)-en-2-yl]ethyl}-3-oxido-7-oxo-7-phenyl-2,4,6-trioxa-3-phosphahept-1-yl benzoate (Example 1, 0.75 mmole, 397 mg) in acetonitrile (15 mL) was added to a solution of sodium tetra borate decahydrate (0.9 mmole, 344 mg), boric acid (3.6 mmole, 223 mg), and sodium chloride (210 mg) in water (30 mL). The reaction mixture was stirred at 45° C. for 10 hours. The reaction mixture was concentrated in vacuo to remove acetonitrile. The remaining phase was neutralized to pH 7 using diluted (1:10) phosphate buffer and then extracted 3 times with methylene chloride (10 mL, 5 mL, 5 mL). The aqueous phase was concentrated in vacuo to a volume of 7 mL and then subjected in 6 aliquots at 1.2 mL each to a preparative HPLC column packed with Primesphere 10 C18, 5×25 cm. Elution was carried out isocratically at 10% acetonitrile in 10 mmole ammonium acetate. Acetonitrile was evaporated from the appropriate fractions collected and the aqueous buffer was freeze-dried to afford 140 mg of the desired compound as a white powder.

MS (ES+): m/e 412 (M+H).

Example 11

[2-(8,9-Dioxo-2,6-diaza-bicyclo[5.2.0]non-1(7)-en-2-yl)-ethyl]-phosphonic acid di-dimethylcarbamoyloxymethyl ester A solution of [2-(8,9-dioxo-2,6-diazabicyclo[5.2.0]non-1 (7)-en-2-yl)ethyl]phosphonic acid (10 mmol, 2.602 g) in dry DMF (130 mL) is treated at ambient temperature with N,N-diisopropylethylamine (40 mmol, 5.17 g) and is stirred for 30 minutes. Dimethyl-carbamic acid chloromethyl ester (30 mmol, 4.14 g) is added to the reaction mixture at ambient temperature and under exclusion of moisture. The reaction mixture is heated to 70° C. and is held with stirring at 70° C. for over 26 hours. The solvent is removed by vacuum distillation and the residue is partitioned (2×) between water and ether. The organic phase is separated, dried over magnesium sulfate, filtered, and evaporated to dryness. The product obtained is flash chromatographed on 200 g silica gel using 8% methanol/chloroform.

Example 12

Evaluation of Compounds of the Present Invention for Treating Pain in Preclinical Models The compounds of the present invention were evaluated for their effectiveness to treat pain. Compound [2-(8,9-dioxo-2, 6-diazabicyclo[5.2.0]non-1(7)-en-2-yl)ethyl]phosphonic acid, a compound of formula (II), was also tested and is reported in Table 1 as Comparative 1. The test methods used herein have been used by others skilled in the art to evaluate the effectiveness of compounds for relieving pain. See e.g., Bennett G J and Xie T K, *A peripheral mononeuropathy in rat produces disorders of pain sensation like those seen in man*, Pain 33: 87-107 (1988); Chaplan S R, Bach R W, Pogrel J W, Chung J M and Yaksh T L, *Quantitative assessment of tactile allodynia in the rat paw*, J. Neurosci. Methods 53: 55-63 (1994); and Mosconi T and Kruger L, *Fixed-diameter polyethylene cuffs applied to the rat sciatic nerve induce a painful neuropathy: ultrastructural morphometric analysis of axonal alterations* Pain 64: 37-57 (1996).

Subjects

Individually housed Sprague-Dawley rats had free access to rat chow and water. A 12-h light/12-h dark cycle was in effect (lights on from 6:00 am to 6:00 pm). Animal maintenance and research were conducted in accordance with the guidelines provided by the National Institutes of Health Committee on Laboratory Animal Resources. These subjects were used in the tests below.

Procedure—Prostaglandin $E_2$-Induced Thermal Hypersensitivity

The terminal 10 cm of the tail was placed into a thermos bottle containing water warmed to 38, 42, 46, 50 or 54° C. The latency in seconds for the animal to remove the tail from the water was used as a measure of nociception. If the animal did not remove the tail within 20 sec, the experimenter removed the tail and a maximum latency of 20 sec was recorded.

Following the assessment of baseline thermal sensitivity, thermal hypersensitivity was produced by a 50 µL injection of 0.1 mg prostaglandin $E_2$ ($PGE_2$) into the terminal 1 cm of the tail. Temperature-effect curves were generated before (baseline) and 30 minutes after the $PGE_2$ injection. Previous studies in other species (e.g., monkeys; Brandt et al., *J. Pharmacol. Exper. Ther.* 296:939, 2001) and results from the current study demonstrate that $PGE_2$ produces a dose- and time-dependent thermal hypersensitivity that peaks 15 min after injection and dissipates after 2 hr.

The ability of compounds to reverse PGE$_2$-induced thermal hypersensitivity was assessed using a single dose time-course procedure. Under this procedure, a single dose of the compound to be tested was administered orally (PO) 10, 30, 100 or 300 min before the injection of PGE$_2$. Tactile sensitivity was assessed 30 min after PGE$_2$ injection.

Data Analysis—The temperature that produced a half-maximal increase in the tail-withdrawal latency (i.e., $T_{10}$) was calculated from each temperature-effect curve. The $T_{10}$ was determined by interpolation from a line drawn between the point above and the point below 10 sec on the temperature-effect curve. For these studies, thermal hypersensitivity was defined as a leftward shift in the temperature-effect curve and a decrease in the $T_{10}$ value. Reversal of thermal hypersensitivity was defined as a return to baseline of the temperature-effect curve and the $T_{10}$ value and was calculated according to the following equation:

$$\% MPE = \frac{(T_{10}^{drug+PGE2}) - (T_{10}^{PGE2})}{(T_{10}^{baseline}) - (T_{10}^{PGE2})} \times 100$$

in which $T_{10}^{drug+PGE2}$ is the $T_{10}$ after a drug in combination with PGE$_2$, $T_{10}^{PGE2}$ is the $T_{10}$ after PGE$_2$ alone, and $T_{10}^{baseline}$ is the $T_{10}$ under control conditions. A % MPE value of 100 indicates a complete return to the baseline thermal sensitivity observed without the PGE$_2$ injection. A value of greater than 100% indicates that the compound tested reduced thermal sensitivity more than the baseline thermal sensitivity without the PGE$_2$ injection.

Results: The compounds of the present invention were effective in reversing PGE$_2$-induced thermal hypersensitivity (Table 1).

TABLE 1

Reversal of PGE$_2$-induced thermal hypersensitivity

| Compound | 10 mg/kg<br>% MPE<br>(±1 SEM)* | 30 mg/kg<br>% MPE<br>(±1 SEM) |
| --- | --- | --- |
| Comparative 1 | −4.7 (10.6)** | 44 (9.5) |
| Example 1 | 57.2 (4.7) | 81 (3.4) |
| Example 2 | 45.6 (13.9) | 76.5 (3.3) |
| Example 3 |  | 87.6 (3.3) |
| Example 4 |  | 78.9 (5.8) |
| Example 5 |  | 55.9 (9.8) |
| Example 6 |  | 16.8 (6.8) |
| Example 7 | 47.0 (12.6) | 77.5 (6.7) |

*SEM is the Standard Error of the Mean.
**The number in parenthesis is the error from the reported % MPE. For example, for Example 1, under a dose of 10 mg/kg, the % MPE value is 57.2 ± 4.7.

What is claimed is:

1. A method for treating pain in a mammal comprising administering to a mammal a therapeutically effective amount of at least one compound of formula (I) or a pharmaceutically acceptable salt thereof:

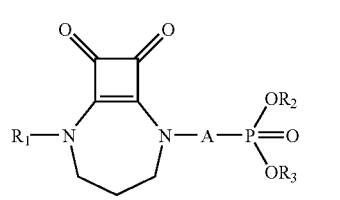

(I)

wherein:
$R_1$ is hydrogen, a $C_1$ to $C_6$ alkyl group, a $C_2$ to $C_7$ acyl group, a $C_1$ to $C_6$ alkanesulfonyl group, or a $C_6$ to $C_{14}$ aroyl group;
A is alkylene of 1 to 4 carbon atoms or alkenylene of 2 to 4 carbon atoms;
$R_2$ and $R_3$ are independently selected from hydrogen, or

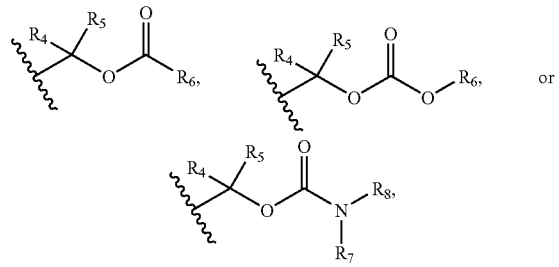

with the proviso that at least one of $R_2$ and $R_3$ is not hydrogen;
$R_4$ and $R_5$ are independently selected from hydrogen, a $C_1$ to $C_4$ alkyl group, a $C_5$ to $C_7$ aryl group, a $C_6$ to $C_{15}$ alkylaryl group having 5 to 7 carbon atoms in the aryl ring, a $C_2$ to $C_7$ alkenyl group, or $C_2$ to $C_7$ alkynyl group, or $R_4$ and $R_5$ may together form a spiro $C_3$ to $C_8$ carbocyclic ring;
$R_6$ is a $C_1$ to $C_{12}$ linear or branched alkyl group, a $C_2$ to $C_7$ linear or branched alkenyl or alkynyl group, a $C_5$ to $C_{13}$ aryl group, a $C_6$ to $C_{21}$ alkylaryl group having 5 to 13 carbon atoms in the aryl moiety; a 5 to 13 membered heteroaryl group, a 6 to 21 membered alkylheteroaryl group having 5 to 13 members in the heteroaryl moiety, a $C_4$ to $C_8$ cycloalkyl group, a $C_5$ to $C_{16}$ alkylcycloalkyl group having 4 to 8 carbon atoms in the cycloalkyl ring;
$R_7$ and $R_8$ are independently selected from hydrogen, a $C_1$ to $C_{12}$ linear or branched alkyl group, a $C_2$ to $C_7$ linear or branched alkenyl or alkynyl group, a $C_5$ to $C_{13}$ aryl group, a $C_6$ to $C_{21}$ alkylaryl group having 5 to 13 carbon atoms in the aryl moiety, a 5 to 13 membered heteroaryl group, a 6 to 21 membered alkylheteroaryl group having 5 to 13 members in the heteroaryl moiety, or $R_7$ and $R_8$ may together form a cycloalkyl or heterocycloalkyl group having in the ring 4 to 8 carbon atoms and optionally one to two atoms selected from nitrogen, oxygen or sulfur;
wherein any $R_1$ to $R_8$ group having an aryl, heteroaryl, cycloalkyl or heterocycloalkyl moiety may optionally be substituted on the aryl, heteroaryl, cycloalkyl or heterocycloalkyl moiety with 1 to about 5 substituents independently selected from a halogen atom, a cyano, nitro or hydroxyl group, a $C_1$-$C_6$ alkyl group, or a $C_1$-$C_6$ alkoxy group.

2. The method of claim 1 wherein the mammal is human.

3. A pharmaceutical composition comprising:
a) a therapeutically effective amount of at least one compound of formula (I) or a pharmaceutically acceptable salt thereof:

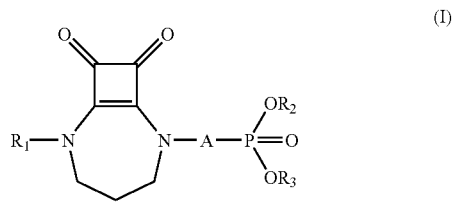

(I)

wherein:

$R_1$ is hydrogen, a $C_1$ to $C_6$ alkyl group, a $C_2$ to $C_7$ acyl group, a $C_1$ to $C_6$ alkanesulfonyl group, or a $C_6$ to $C_{14}$ aroyl group;

A is alkylene of 1 to 4 carbon atoms or alkenylene of 2 to 4 carbon atoms;

$R_2$ and $R_3$ are independently selected from hydrogen, or

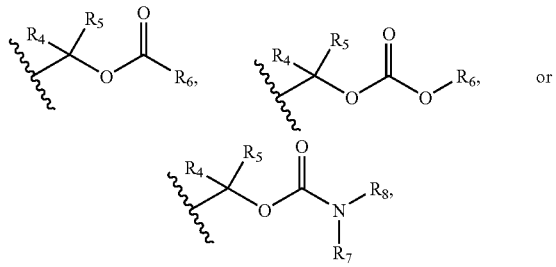

with the proviso that at least one of $R_2$ and $R_3$ is not hydrogen;

$R_4$ and $R_5$ are independently selected from hydrogen, a $C_1$ to $C_4$ alkyl group, a $C_5$ to $C_7$ aryl group, a $C_6$ to $C_{15}$ alkylaryl group having 5 to 7 carbon atoms in the aryl ring, a $C_2$ to $C_7$ alkenyl group, or $C_2$ to $C_7$ alkynyl group, or $R_4$ and $R_5$ may together form a Spiro $C_3$ to $C_8$ carbocyclic ring;

$R_6$ is a $C_1$ to $C_{12}$ linear or branched alkyl group, a $C_2$ to $C_7$ linear or branched alkenyl or alkynyl group, a $C_5$ to $C_{13}$ aryl group, a $C_6$ to $C_2$, alkylaryl group having 5 to 13 carbon atoms in the aryl moiety; a 5 to 13 membered heteroaryl group, a 6 to 21 membered alkylheteroaryl group having 5 to 13 members in the heteroaryl moiety, a $C_4$ to $C_8$ cycloalkyl group, a $C_5$ to $C_{16}$ alkylcycloalkyl group having 4 to 8 carbon atoms in the cycloalkyl ring;

$R_7$ and $R_8$ are independently selected from hydrogen, a $C_1$ to $C_{12}$ linear or branched alkyl group, a $C_2$ to $C_7$ linear or branched alkenyl or alkynyl group, a $C_5$ to $C_{13}$ aryl group, a $C_6$ to $C_{21}$ alkylaryl group having 5 to 13 carbon atoms in the aryl moiety, a 5 to 13 membered heteroaryl group, a 6 to 21 membered alkylheteroaryl group having 5 to 13 members in the heteroaryl moiety, or $R_7$ and $R_8$ may together form a cycloalkyl or heterocycloalkyl group having in the ring 4 to 8 carbon atoms and optionally one to two atoms selected from nitrogen, oxygen or sulfur;

wherein any $R_1$ to $R_8$ group having an aryl, heteroaryl, cycloalkyl or heterocycloalkyl moiety may optionally be substituted on the aryl, heteroaryl, cycloalkyl or heterocycloalkyl moiety with 1 to about 5 substituents independently selected from a halogen atom, a cyano, nitro or hydroxyl group, a $C_1$-$C_6$ alkyl group, or a $C_1$-$C_6$ alkoxy group; and b) at least one pharmaceutically acceptable carrier.

4. The composition of claim 3 wherein $R_1$ is H or a $C_1$ to $C_4$ alkyl group;

A is an alkylene group having the formula —$(CH_2)_n$—, where n is 1 to 3;

$R_2$ and $R_3$ are independently selected from H or:

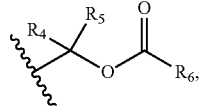

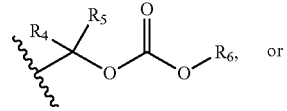

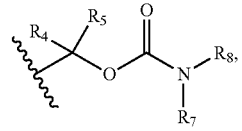

with the proviso that at least one of $R_2$ and $R_3$ is not H;

$R_4$ and $R_5$ are independently selected from H or a C1 to C4 alkyl group; and $R_6$ is selected from a $C_3$ to $C_{10}$ linear or branched alkyl group, a $C_5$ to $C_7$ aryl group, a 5- to 7-membered heteroaryl group, or a cycloalkyl group having in the ring 5 to 7 carbon atoms.

5. The composition of claim 4 wherein $R_2$ and $R_3$ are independently selected from H or the moiety (B) and $R_6$ is a $C_5$ to $C_7$ aryl group.

6. The composition of claim 3 wherein the compound of formula (I) is selected from:

a) 3-{2-[8,9-dioxo-2,6-diazabicyclo[5.2.0]non-1(7)-en-2-yl]ethyl}-3-oxido-7-oxo-7-phenyl-2,4,6-trioxa-3-phosphahept-1-yl benzoate;

3-{2-[8,9-dioxo-2,6-diazabicyclo[5.2.0]non-1(7)-en-2-yl[ethyl]-3-oxido-7-oxo-8-propyl-2,4,6-trioxa-3-phosphaundec-1-yl-2-propylpentanoate;

c) 2,2-dimethyl-propionic acid {(2,2-dimethyl-propionyloxymethoxy)-[2-(8,9-dioxo-2,6-diaza-bicyclo[5.2.0]-non-1(7)-en-2-yl)-ethyl]-phosphinoyloxy}methyl ester;

d) 7-cyclohexyl-3-{2-[8,9-dioxo-2,6-diazabicyclo[5.2.0]non-1(7)-en-2-yl]ethyl)-1,5-dimethyl-3-oxido-7-oxo-2,4,6-trioxa-3-phosphahept-1-yl cyclohexanecarboxylate;

e) 7-cyclohexyl-3-{2-[8,9-dioxo-2,6-diazabicyclo[5.2.0]non-1(7)-en-2-yl]ethyl-3-oxido-7-oxo-2,4,6-trioxa-3-phosphahept-1-yl cyclohexanecarboxylate;

f) [2-(8,9-Dioxo-2,6-diaza-bicyclo[5.2.0]non-1-(7)-en-2-yl)-ethyl]-phosphonic acid diisopropoxycarbonyl oxymethyl ester;

g) [2-[8,9-dioxo-2,6-diazabicyc[5.2.0]non-1(7)-en-2-yl]ethyl]-phosphonic acid bis[1-(benzoyloxy)ethyl]ester;

h) benzoic acid [2-(8,9-dioxo-2,6-diaza-bicyclo[5.2.0]non-1(7)-en-2-yl)-ethyl]-hydroxy-phosphinoyloxymethyl ester; or i) [2-(8,9-Dioxo-2,6-diaza-bicyclo[5.2.0]non-1(7)-en-2-yl)-ethyl]-phosphonic acid di-dimethylcarbamoyloxymethyl ester; or a pharmaceutically acceptable salt thereof.

* * * * *